(12) United States Patent
Seo et al.

(10) Patent No.: US 7,217,770 B2
(45) Date of Patent: May 15, 2007

(54) STABLE POLYMERIC MICELLE-TYPE DRUG COMPOSITION AND METHOD FOR THE PREPARATION THEREOF

(75) Inventors: Min-Hyo Seo, Daejeon (KR); Yil-Woong Yi, Daejeon (KR); Jae-Won Yu, Daejon (KR)

(73) Assignee: Samyang Corporation, Seoul (KR)

( * ) Notice: Subject to any disclaimer, the term of this patent is extended or adjusted under 35 U.S.C. 154(b) by 582 days.

(21) Appl. No.: 10/276,499

(22) PCT Filed: May 17, 2000

(86) PCT No.: PCT/KR01/00802

§ 371 (c)(1), (2), (4) Date: Nov. 15, 2002

(87) PCT Pub. No.: WO01/87345

PCT Pub. Date: Nov. 22, 2001

(65) Prior Publication Data

US 2003/0143184 A1    Jul. 31, 2003

(30) Foreign Application Priority Data

May 17, 2000   (KR) ................... 10-2000-26359

(51) Int. Cl.
*C08F 283/00* (2006.01)
*C08G 63/91* (2006.01)
*C08G 69/48* (2006.01)
*A61K 31/74* (2006.01)
*A61K 38/13* (2006.01)

(52) U.S. Cl. .............. 525/419; 525/420; 528/354; 528/355; 424/78.17; 514/449; 514/283; 514/11; 514/34; 514/182; 514/27; 514/50

(58) Field of Classification Search ............ 525/419, 525/420; 528/354, 355; 424/18.17; 514/449, 514/283, 11, 34, 182, 27, 50
See application file for complete search history.

(56) References Cited

U.S. PATENT DOCUMENTS 5,470,944 A * 11/1995 Bonsignore .......... 528/354
5,683,723 A    11/1997 Spenlehauer et al.
5,702,717 A    12/1997 Cha et al.
5,877,205 A     3/1999 Andersson
5,922,754 A     7/1999 Burchett
6,322,805 B1 * 11/2001 Kim et al. .......... 424/426
6,375,952 B1 *  4/2002 Koelle et al. ......... 424/186.1

FOREIGN PATENT DOCUMENTS

EP    0645145 B1    12/1997

OTHER PUBLICATIONS

Kim et al in Polymers for advanced technologies, vol. 10, pp. 647-654 (1999).*
Kim et al in Polym. prepa. (Am. Chem. Soc., Div. Polym. Chem) vol. 39 (2), pp. 130-131, 1998.*
K. Kataoka, Design of nanoscopic vehicles for drug targeting based on micellization of amphipilic block copolymers, J. Macromol. Sci.-Pure Appl. Chem A31 (1994) 1759-1769.
H. Maeda, The tumor blood vessel as an ideal target for macromolecular anticancer agents, J. Control. Rel. 19(1992) 315-324.
Marie-Christine Jones, Jean-Christophe Leroux, Polymeric micelles—a new generation of colloidal drug carriers, European Journal of Pharmaceuticals and Biopharamceutics 48 (1999) 101-111.
Xichen Zhang, John K. Jackson, Helen M. Burt, Development of amphiphilic diblock copolymers as micellar carriers of taxol, International Journal of Pharmaceutics 132 (1996) 195-206.

* cited by examiner

*Primary Examiner*—Duc Truong
(74) *Attorney, Agent, or Firm*—Thorpe North & Western, LLP

(57) ABSTRACT

A biocompatible stable composition containing a hydrophobic drug, such as paclitaxel. The composition, which forms a syringeable polymeric micellar solution in aqueous or body fluids, is a freeze-dried product comprising a hydrophobic drug, i.e. paclitaxel, and an amphiphilic block copolymer wherein a hydrophobic group having affinity or attraction with the hydrophobic drug, such as paclitaxel, is incorporated on its end.

42 Claims, 3 Drawing Sheets

US 7,217,770 B2

STABLE POLYMERIC MICELLE-TYPE DRUG COMPOSITION AND METHOD FOR THE PREPARATION THEREOF

This application is based on PCT/KR01/00802, which claims priority, based on a Korean patent application No. 2000-26359 filed May 17, 2000.

TECHNICAL FIELD

The present invention relates to a biocompatible and stable polymeric drug composition capable of forming a micelle in an aqueous environment, said composition comprising an amphiphilic block copolymer of a hydrophilic poly(alkylene glycol) component and a hydrophobic biodegradable component wherein the hydrophobic biodegradable component of the copolymer is capped with a modifying group having an affinity or attraction for a hydrophobic drug, and wherein a hydrophobic drug is physically trapped in the hydrophobic core of the micelle. This micelle-forming composition can solubilize the hydrophobic drug in a hydrophilic environment forming a stable hydrophobic drug-containing micellar solution.

BACKGROUND ART

Many important drugs are hydrophobic and have limited solubility in water. In order to attain the expected therapeutic effects of such drugs, it is usually required that a solubilized form of the drug be administered to a patient. For this purpose there have been developed a number of methods which are based on the use of: auxillary solvents; surfactants; soluble forms of the drug, e.g., salts and solvates; chemically modified forms of the drug, e.g., prodrugs; soluble polymer-drug complexes; special drug carriers such as liposomes; and others. Each of the above methods is hampered by one or more particular problems, e.g., the method based on the use of a surfactant to solubilize hydrophobic drugs has problems in that most surfactants are relatively toxic and precipitation of the hydrophobic drug occurs when subjected to dilution. European Patent EP 0645145 discloses a method of solubilizing a typical poorly water soluble drug, paclitaxel, by use of Cremophor EL™, a polyoxyethylene castor oil derivative. The use of these surfactants, however, is restricted due to toxic side effects such as hypersensitivity. They have limitations in that their poor ability to stabilize micelles can cause precipitation of the drug when the micellar solution is either stored or is to remain in place for an extended period of time.

In recent years, polymeric micelles have been investigated as potential carriers for poorly water soluble drugs. Efforts have been made for the preparation, characterization and pharmaceutical application of polymeric micelles. For example, see M. Jones, et al., Polymeric micelles—a new generation of colloidal drug carriers, *Eur. J. Pharm. Biopharm.* 48(1999) 101–111. Polymeric micelles provide attractive characteristics in two major aspects: (a) they can solubilize poorly water soluble, or hydrophobic drugs in their hydrophobic inner core; and (b) they can avoid uptake of the drug by the RES (reticuloendothelial system) or the MPS (mononuclear phagocytes system) in vivo.

Polymeric micelles are characterized by a core-shell structure in aqueous media that results from the amphiphilic block copolymers having hydrophobic (core) and hydrophilic (shell) segments. A poorly water soluble drug is entrapped within the hydrophobic core of the micelle. There has been considerable research in the development of A-B, A-H-A, or B-A-B block copolymers having a hydrophilic A block and a hydrophobic B block. As a drug carrier, it is preferred that the hydrophobic B(inner micelle core block) comprises a biodegradable polymer such as poly-DL-lactide, poly-ε-caprolactone or poly(γ-benzyl-L-aspartate) and the hydrophilic A (outer micelle shell block) be a polymer such as polyethylene glycol which is capable of interacting with plasma proteins and cell membranes.

Polymeric micelles can provide for prolonged systemic circulation time due to their small size (<100 nm), their hydrophilic shell which minimizes uptake by the MPS, and their high molecular weight which prevents renal excretion (K. Katasoka, Design of nanoscopic vehicles for drug targeting based on micellization of amphiphilic block copolymers, *J. Macromol. Sci.—Pure Appl. Chem* A31(1994) 1759–1769). Additionally, H. Maeda showed experimental evidence supporting the enhanced permeability and retention (EPR) effect of macromolecules in cancer chemotherapy. The tumor vessels are more leaky and less permiselective than normal vessels, and accumulation of polymeric micelles in tumors is explained by this increased vascular permeability and the lack of lymphatic drainage in tumors (H. Maeda, The tumor blood vessel as an ideal target for macromolecular anticancer agents, *J. Control. Rel.* 19(1992) 315–324).

Among various pharmaceutical applications of polymeric micelles, research has been focused on the parenteral administration of anticancer drugs using polymeric micelles because of the above-described advantages, such as a long circulation time in vivo, and drug targeting by the EPR effect.

Taxanes, including paclitaxel and its analogues, that exert antitumor activity due to inhibition of cell proliferation by preventing microtuble assembly, are promising anticancer agents and their preparation methods and application for chemotherapy have been widely studied. They are now available from various routes of supply such as extraction from the bark or needles of the pacific yew tree, biological method of tissue culture, or chemical synthesis. Since paclitaxel is practically insoluble in water (solubility of less than 0.01 mg/mL), several compositions to solubilize or disperse the drug in infusion fluid have been proposed for parenteral administration to patients. Bristol-Myers Squibb introduced an injectable composition containing paclitaxel, Taxol®, and this formulation is the only one which has been approved for human use by the FDA. Taxol® is a solution in which a mixture of paclitaxel and polyethoxylated castor oil (Cremophor® EL, BASF Aktiengesolischaft) is dissolved in alcohol. However, Cremophor® EL has a potential for inducing various side effects including anaphylactic reactions. Additionally, the Cremophor® EL in the Taxol® formulation causes the leaking of harmful plasticizers into the infusion fluid from the infusion bags or plastic tubes.

Intensive studies have been made in an effort to overcome the shortcomings of the Taxol® formulation, and as a result, several compositions containing paclitaxel are known as substitutes for the Taxol® formulation. U.S. Pat. No. 5,877, 205 discloses a composition formulated in such a manner that pacilataxel is dissolved in an organic solvent followed by addition of secondary solvent to stabilize the drug in solution for subsequent final dilution in an aqueous lipid emulsion. U.S. Pat. No. 5,922,754 discloses another composition comprising paclitaxel, an acid, water, and mixture of some organic solvents such as triacetin, alcohol, and Solutol™ (BASF, polyethylene glycol ester of 12-hydroxystearic acid).

Although the solution of the above formulation is stable and does not precipitate for more than 72 hours (3 days) at room temperature while the solution of the Taxol® formulation is stable for 27 hours, there is an important limitation to their use in the body because the formulations still contain organic solvents, such as dimethyl acetamide, or excess amounts of Solutol™ ($LD_{50}$[mouse, iv] of Polyoxyl 20 Stearate=0.87 g/kg), which is more toxic than Cremophor EL ($LD_{50}$[mouse, iv]=2.5 g/kg). [$LD_{50}$ from *Handbook of Pharmaceutical Exipients,* 2nd ed., American Pharmaceutical Association].

Therefore, while polymeric micelles seem to be one of the most advantageous carriers for the delivery of poorly water soluble drugs, such as paclitaxel or other anti-cancer agents, problems remain due to their lack of stability in infusion fluid or body fluid. X. Zhang et al, reported that a diblock copolymer of polylactide and monomethoxypolyethylene glycol(mPEG) was useful as a carrier of paclitaxel (X. Zhang et al. Development of amphiphilic diblock copolymers as micellar carriers of taxol, *Int. J. Pharm.* 132(1996) 195–206). The formulation dissolves paclitaxel by incorporating the drug into a polymeric micelle in aqueous media. This formulation has an advantage in that the materials employed in this formulation are non-toxic and their hydrolysis products are easily eliminated from the body, thus, overcoming prior art shortcomings in compositions containing paclitaxel, such as the Taxol® formulation, and formulations shown in U.S. Pat. Nos. 5,877,205 and 5,922,754. The formulation shown in Zhang et al., however, still has a disadvantage in that, due to unstable micellar formation, the drug is precipitated from the micelle into the aqueous infusion fluid within 48 hours.

Although polymeric micelles would seem to be ideal carriers for poorly water soluble drugs because of their distinct advantages, such as small size, high solubility, simple sterilization, controlled release of drugs, the physical stability of such carriers limits their application for pharmaceutical use.

SUMMARY OF THE INVENTION

The present invention provides an improved, stable, hydrophobic drug containing polymeric micelle in an aqueous media. The composition of the present invention can be stored for longer than three years in a sterilized container, without any denaturation of the compounds and the polymeric micelles formed in the aqueous infusion fluid of the present invention are stable for longer than 72 hours (3 days). In addition, the formulation of the present invention causes no side effects to a patient and intravascular administration of the formulation provides improved bioavailability with high plasma concentration of the drug, e.g. paclitaxel, being achieved.

The present invention provides a stable biodegradable polymeric micelle-type drug composition which comprises: a modified biodegradable polymeric drug carrier micelle having a hydrophobic drug physically trapped within, but not covalently bonded to the drug carrier micelle. The micelle is capable of dissolving in water to form a stable, injectable solution thereof. The drug carrier micelle comprises an amphiphilic block copolymer having a hydrophilic poly(alkylene glycol) A block component, and a biodegradable hydrophobic polymer B block component selected from the group consisting of poly(lactic acid), poly(glycolic acid), poly(lactic-co-glycolic acid), poly(ε-caprolactone), and wherein the amphiphilic block copolymer has terminal ends modified by end groups that have an attraction or affinity for the hydrophobic drug contained in the micelle core.

The present invention also provides a method for preparing a pharmaceutical composition, which comprises the following steps: 1) preparing an amphiphilic block copolymer modified to have end groupings which have an affinity or attraction to a hydrophobic drug; 2) preparing a drug-polymer matrix by dissolving a hydrophobic drug and the modified block copolymer in an organic solvent followed by evaporation of the solvent; 3) preparing an aqueous micellar solution by dissolving the drug/modified polymer matrix in water; and 4) preparing a final formulation by freeze-drying the micellar solution followed by appropriate sterilization.

Therefore, the present invention provides for biocompatible, stable, drug containing compositions capable of forming syringeable polymeric micellar solutions in aqueous or body fluids. The composition of the present invention is a freeze-dried product comprising a hydrophobic drug (e.g. paclitaxel) and an amphiphilic block copolymer wherein hydrophobic drug attracting groups are incorporated on its ends. The composition of the present invention also provides i) a shelf life of longer than three years in a sterilized container, ii) stability of longer than three days in an infusion fluid, iii) minimal side effects due to no use of any toxic excipients or organic solvents, and iv) improved bioavailability indicated by the high concentration of the hydrophobic drug such as paclitaxel achieved in plasma.

Additional features and advantages of the invention will be apparent from the detailed description which follows, taken in conjunction with the accompanying examples, which together illustrate, features of the invention.

DETAILED DESCRIPTION OF THE INVENTION

Figure 1:
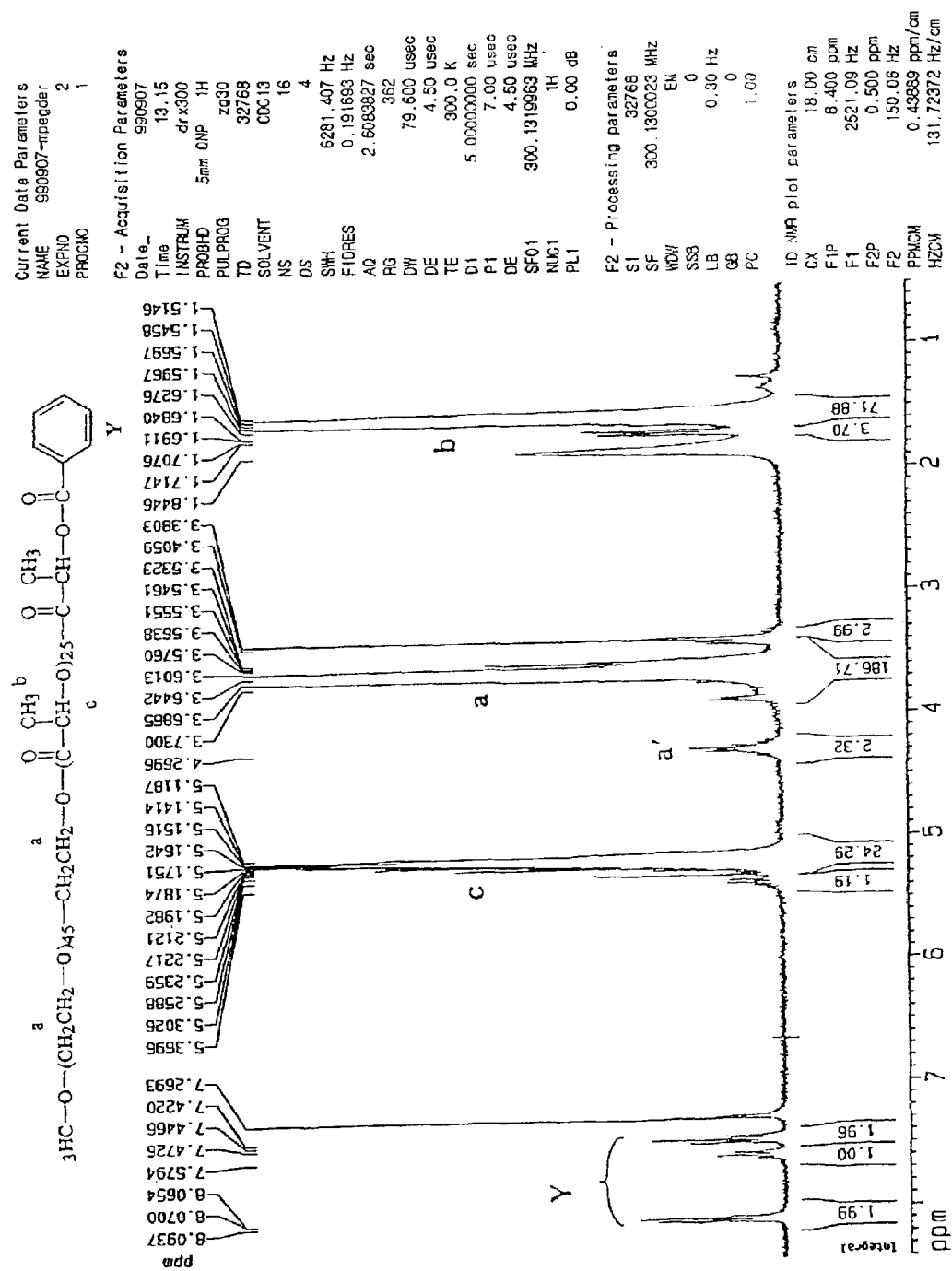
FIG. 1 is the NMR spectrum of mPEG—PLA—Bz.

Reference will now be made to the exemplary embodiments and specific language will be used herein to describe the same. It will nevertheless be understood that no limitation of the scope of the invention is thereby intended. Alterations and further modifications of the inventive features illustrated herein, and additional applications of the principles of the invention as illustrated herein, which would occur to one skilled in the relevant art and having possession of this disclosure, are to be considered within the scope of the invention.

The amphiphilic block copolymer micelle composition of the present invention is very effective in solubilizing hydrophobic drugs by way of physically incorporating them within the micelle and improving the stability of the drug by means of the affinity or attraction provided by the end group modifications to the copolymer. The resulting biodegradable polymeric micelle composition containing the hydrophobic drug is soluble in water forming a solution that is suitable for sustained-release of the drug in vivo, thereby enhancing the therapeutic effect of the drug. Such therapeutic effect may be maximized by controlling the molecular weights and the relative ratios of the hydrophilic and hydrophobic blocks. Moreover, the composition of the present invention can be stored for longer than three years in a sterilized container without any denaturation of the components and the polymeric micelles formed in the aqueous infusion fluid of the present invention are stable for longer than 72 hours (3 days). In addition, the formulation of the present invention causes minimal or no side effects to a patient and intravascular administration of the formulation provides for improved bioavailability with high plasma concentrations of the drug being achieved.

The biodegradable polymeric micelle-type drug composition of the present invention, which is capable of forming stable polymeric micelles in aqueous or body fluids, is comprised of a biodegradable modified amphiphilic block copolymer having physically entrapped therein one or more hydrophobic drugs, and when administered, the hydrophobic biodegradable polymer decomposes in vivo by simple hydrolysis into non-toxic small molecules.

The modified amphiphilic block copolymer comprises a hydrophilic poly(alkylene glycol) component and a hydrophobic biodegradable polymer component. The polyalkylene glycol suitable for the hydrophilic component in the block copolymer of the present invention is a member selected from the group consisting of polyethylene glycol, monoalkoxy polyethylene glycol and monoacyloxy polyethylene glycol, wherein the molecular weight of the polyalkylene glycol is preferably within the range of 200~20,000 Daltons and more preferably, within the range of 1,000~15,000 Daltons.

The hydrophobic biodegradable polymer component of the copolymer of the present invention is a member selected from the group consisting of polylactides, polycarprolactone, copolymers of lactide and glycolide, copolymers of lactide and carprolactone, copolymers of lactide and 1,4-dioxan-2-one, polyorthoesters, polyanhydrides, polyphosphazines, poly(amino acid)s and polycarbonates. Preferably, the hydrophobic biodegradable polymer component of the copolymer of the present invention is a member selected from the group consisting of polylactides, polycaprolactone, a copolymer of lactide and glycolide, a copolymer of lactide and caprolactone, and a copolymer of lactide and 1,4-dioxan-2-one. The molecular weight of the hydrophobic biodegradable polymer component is preferably within the range of 500~20,000 Daltons and more preferably within the range of 1,000~10,000 Daltons.

As will be more fully described in connection with Formula I that follows, the hydroxy group conventionally found at the end of a hydrophilic polyalkylene glycol can be blocked or capped by a $C_1$-$C_4$ alkyl group thereby forming an ether capping, such as is found in monomethoxy polyalkylene glycols (mPEG) or by a $C_1$-$C_4$ acyl thereby forming an ester capping, such as is found in monoacyloxy polyalkylene glycols. The hydroxyl group at the end of a hydrophobic polymer block, such as a polylactide, is capped by acylation thereby forming an ester capping wherein the acyl group contains from 2 to 10 carbon atoms such as an alkyl, aryl, alkaryl or aralkyl group as will be more fully explained. Preferably, the end capping of the hydrophilic block will be by a methoxy group and the end capping of the hydrophobic block will be by an acetyloxy or benzoyloxy group.

The amphiphilic block copolymers can be prepared according to methods described in U.S. Pat. Nos. 5,683,723 and 5,702,717, hereby fully incorporated by reference. For example they may be prepared via ring opening bulk polymerization of one of the monomers, such as a lactide, caprolactone, 1,4-dioxan-2-one, or a glycolide, with a polyethylene glycol derivative in the presence of stannous octoate as a catalyst. Block copolymers having a poly(amino acid) block are prepared by the reaction of an amino acid N-carboxy anhydride with a polyethylene glycol derivative.

The hydrophilic polyethylene glycol block is preferably in the range of 30~70% by weight of the block copolymer, and most preferably 40~60% by weight.

The improved stability attributable to the present invention is by means of modifying the block copolymer such that at least one end of the end terminal groups has an affinity or attraction with a hydrophobic drug, which significantly improves the stability of the micelles and the drugs entrapped therein.

Any drug having a water solubility of less than 10 mg/ml can be used as the "hydrophobic drug" or "poorly water soluble drug" to be incorporated in the polymeric micelles of the present invention. Examples of hydrophobic drugs that can be used include anticancer agents, antiinflammatory agents, antifungal agents, antiemetics, antihypertensive agents, sex hormones, and steroids. Typical examples of the hydrophobic drugs are anticancer agents such as paclitaxel, taxotane, camptothecin, doxorubicin, daunomycin, cisplatin, 5-fluorouracil, mitomycin, methotrexate, and etoposide; antiinflammatory agents such as indomethacin, ibuprofen, ketoprofen, flubiprofen, dichlofenac, piroxicam, tenoxicam, naproxen, aspirin, and acetaminophen; antifungal agents such as itraconazole, ketoconazole, amphotericin; sex hormones such as testosterone, estrogen, progestone, and estradiol; steroids such as dexamethasone, prednisodone, and triameinolene; antihypertensive agents such as captopril, ramipril, terazosin, minoxidil, and parazosin; antiemetics such as ondanseiron, and granisetron; antibiotics such as metronidazole, and fusidic acid; cyclosporine; prostagladins; and biphenyl dimethyl dicarboxylic acid. The present invention is particularly useful for administering anti-cancer drugs such as paclitaxel, taxotane, doxorubicin, cisplatin, carboplatin, 5-FU, etoposide, and camptothecin; sex hormones such as testosterone, estrogen, and estradiol; antifungal agents such as itraconazole, ketoconazole, and amphotericin; steroids such as triamoinolone acetonide, hydrocortisone, dexamethasone, prednisolone, and betamethasone; cyclosporine; and prostagladins. The hydrophobic drug may be incorporated in the polymeric micelle composition up to 50 wt % based on the total weight of the block copolymer and the drug.

One embodiment of the present invention provides a pharmaceutical composition, which is capable of forming a stable polymeric micelle in aqueous or body fluids. comprising:

a) a taxane analog; and b) b) a block copolymer which is represented by formula (I) below:

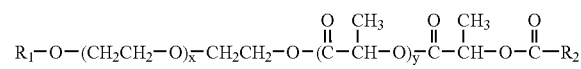

wherein $R_1$ is H, a $C_1$ to $C_4$ alkyl, a $C_1$ to $C_4$ acyl or

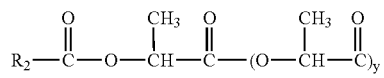

wherein $R_2$ is a $C_1$ to $C_9$ alkyl, aryl, alkaryl or aralkyl groups; x is an integer of 20–300, and y is an integer of 15–70.

Representatives of alkyl groups are methyl, ethyl, propyl, and butyl. Representative of an aryl group is phenyl as well as functionally equivalent heterocyclic groups such as thienyl, furyl, pyridinyl groups and the like. Representative of an aralkyl grouping is benzyl and representative of an alkaryl group is tolyl. Preferably $R_1$ is a methyl group and $R_2$ is methyl or phenyl group.

The block copolymer of the present invention can be prepared via ring opening bulk polymerization of heterocyclic ester compounds (lactones), such as DL-lactide, glycolide, ε-caprolactone, or p-dioxanone, with polyethylene glycol or monomethoxy polyethylene glycol in the presence of stannous octoate. At least one terminal ends of the copolymer is capped in the manner described with a group such as benzoyl or acetyl group having affinity or attraction for a hydrophobic drug such as paclitaxel. One example of the resultant block polymer of this invention is represented by formula (I). Methods of adding an end group to the end of block copolymer were described in the "Preparation Examples 1a, 1b, and 2":

[For a benzoyl group]
mPEG+DL-lactide→mPEG—PLA—OH (block copolymer having hydroxyl group)
mPEG—PLA—OH+Cl—(C=O)—$C_6H_5$ (benzoyl chloride)→
mPEG—PLA—O—(C=O)—$C_6H_5$ (block copolymer having a benzoyloxy group)

[For an acetyl group]
mPEG—PLA—OH+Cl—(C=O)—$CH_3$ (acetyl chloride)→
mPEG—PLA—O—(C=O)—$CH_3$ (block copolymer having an acetyloxy group)

In this case, the block copolymer and the end group are linked by an ester bond [—O—(C=O)—], and can be expressed as mPEG—PLA—O—(C=O)—R, where R could be $CH_3$, $C_6H_5$, ethyl, propyl, or others.

An alternative method to modify the block copolymer of the present invention is by using isocyanate;
mPEG—PLA—OH+O=C=N—$CH_2CH_3$ (ethyl isocyanate)→
mPEG—PLA—O—(C=O)—NH—$CH_2CH_3$ (block copolymer having an ethyl carbamoyloxy group), or
mPEG—PLA—OH+O=C=N—$C_6H_5C$(=O)—O—$CH_3$ (methyl isocyantobenzoate)→
mPEG—PLA—O—(C=O)—NH—$C_6H_5C$(=O)—O—$CH_3$ (block copolymer having a methoxycarbonyl phenyl carbamoyloxy group)

In this case, the block copolymer and the end group are linked by a carbamate(urethane) bond [—O—(C=O)—N—], and can be expressed as mPEG—PLA—O—(C=O)—NH—R, wherein R is a $C_1$ to $C_9$ member selected from the group consisting of alkyl, aryl, alkaryl and aralkyl groups. Representatives of alkyl groups are methyl, ethyl, propyl, and butyl groups. Representative of an aryl group is phenyl as well as functionally equivalent heterocyclic groups such as thienyl, furyl, pyridinyl, and the like. Representative of an aralkyl group is benzyl and representative of an alkaryl group is tolyl. Preferably $R_1$ is a methyl group and $R_2$ is a methyl or phenyl group.

Illustratively, the copolymer (10~200 mg) prepared as described is then dissolved in an organic solvent (1~5 mL) such as acetonitrile, dichloromethane, or tetrahydrofuran (THF). A poorly water soluble drug (2~50 mg) such as paclitaxel, is dissolved in the same organic solvent, and then mixed with the polymer solution. A homogeneous drug-polymer matrix is obtained by evaporating the organic solvent at an elevated temperature. The drug-polymer matrix is dissolved in water to produce an aqueous micellar solution at a polymer concentration higher than the critical micelle concentration (CMC). The polymeric micelle having a spherical shape in aqueous media consists of two different regions, a hydrophobic inner core and a hydrophilic outer shell. This particular structure is due to the amphiphilic properties of the polymer which consists of a hydrophobic polylactone block and a hydrophilic polyethylene glycol block. The hydrophobic drug, such as paclitaxel, is trapped in the inner core of the spherical micelle. The stable micellar composition containing paclitaxel, in the hydrophobic core formed by the hydrophobic segments of the copolymer, is prepared by freeze-drying the aqueous micellar solution.

The freeze-dried composition pared by the above-mentioned method can be diluted in an aqueous media, such as 0.9% sodium chloride (normal saline), 5% dextrose, 5% dextrose and 0.9% sodium chloride, or 5% dextrose in Ringer's solution, to achieve a final paclitaxel concentration of 0.1~3.0 mg/mL, more preferably 0.2~1.5 mg/mL. The diluted solution is placed in a thermostat at 25° C. At predetermined time intervals, 0.5 mL of the solution is taken out with a syringe and filtered through a 0.45 μm PVDF syringe filter (Milipore, Cat No. SLHV004NL). The drug concentration in the filtered solution is then determined by high performance liquid chromatography (HPLC) assay.

Paclitaxel is traditionally administered at a dose of about 175 mg/m². For a human adult with 70 Kg body weight, the surface area and the total blood volume are about 1.8 m² and 5 L, respectively. When paclitaxel is administered by one bolus intravenous injection at the indicated dose, initial plasma concentrations of paclitaxel are in the range of 0.04~0.08 mg/mL. Therefore, the stability test for a diluted concentration of 0.04~0.08 g/mL is also carried out at body temperature (37° C.).

The HP1100 series HPLC system (Hewlett-Packard) is used for determination of the drug concentration. Peak detection and integration is performed with HP Chemstation for LC Rev.A.06.01. Chromatographic separation is achieved with 00G-4012-E0 (Phenomenex) column (250× 4.6 mm, 5 μm). Paclitaxel and the internal standard were eluted with the mobile phase of actonitrile-water (45:55, v/v) using a flow rate of 1.5 mL/min. Ultraviolet (UV) analysis was performed at a wavelength of 227 nm. Propyl-p-hydroxybenzoate was used for the internal standard.

The terminal end capping groups in the block copolymer play an important role in the stability of the hydrophobic drug trapped in the core region of the micelle formed in aqueous media. The formulations employing the diblock copolymers of polyethylene glycol and polylactone which do not have the ends capped with groups having an attraction or affinity for the hydrophobic drug have a drawback in that the drug is precipitated from the micelle into the aqueous infusion fluid within 48 hours due to unstable micellar formation. In order to overcome the precipitation of a drug in the infusion fluid, the block copolymer of the present invention was modified terminal hydroxyl groups that are capped with a group which has affinity or attraction for the hydrophobic drug. Thus, the hydrophobic drug remains in the hydrophobic core of the micelle for a longer period of time due to the affinity or attraction between the drug and the terminal end capping group of the polymer. As a result, the composition provides long-term stability for infusion therapy. Furthermore, the pharmaceutical composition of the present invention incorporates paclitaxel up to 40% by weight.

Traditionally, prior art formulations are supplied as a concentrated solution composition in organic solvents, and they are diluted in aqueous media before use. On the contrary, the final formulation of the present invention is a freeze-dried composition in a sterilized container. It is easily dissolved to a concentration of 0.1~3.0 mg/mL, more preferably 0.2~1.5 mg/mL, in an appropriate conventional injection fluid prior to infusion. As the composition contains no solvents and is stored in a very stable freeze-dried solid state, the composition of the present invention eliminates any possible denaturation or precipitation of the drug by temperature changes during storage, that is, the composition provides a longer shelf life than those in the prior art.

The polymeric micellar solution of the present invention is stable with no precipitation in the infusion fluid for longer than 72 hours (3 days) at room temperature (25° C.). When the composition is diluted to a concentration of paclitaxel of 0.04~0.08 mg/mL, i.e. initial plasma concentration after one bolus iv injection of the recommended dose of Taxol® inj., the composition is more stable than the compositions formulated with the polymers not having the above-described terminal end capping groups. Furthermore, the composition of the present invention improves the paclitaxel plasma concentration in pharmacokinetic experiments with rats, as described below.

The formulation of the present invention does not contain any potentially harmful material for use in the human body, such as an organic solvent or Cremophor EL which induce various side effects. The polymers incorporated in the composition are biocompatible, they are already approved for use in the human body from the FDA, and their hydrolysis products are easily eliminated from the body.

A pharmacokinetic experiment was performed with Sprague-Dawley rats having a body weight of 200~250 g. The freeze-dried composition formulated by the above-mentioned method was dissolved in normal saline to give a paclitaxel concentration of 1.0 mg/mL and the formulation was injected into the tail vein with the does of paclitaxel given being 20 mg/kg. At specified time intervals, blood samples were drawn in heparinized tubes from the tail vein. They were centrifuged at 2000 rpm for 5 minutes for separation. The internal standard, biphenyl dimethyl dicarboxylate, was added to the separated plasma for HPLC assay. The drug was extracted from the plasma using ethyl acetate, and dried by evaporation of the solvent. The dried product was dissolved in actonitrile-water and the paclitaxel plasma concentration was determined by HPLC as described above. A standard solution was prepared by dissolving a known amount of paclitaxel in the plasma, acetonitrile, and the internal standard. The HPLC assay for the stability test was performed with the above-described HPLC system. Chromatographic separation was achieved with a VYDAC (Hesperia) 218MR54 C18 column (250×4.6 mm, 5 µm). Paclitaxel and the internal standard were eluted with the mobile phase of actonitrile-water, with a linear gradient from 30:70 (v/v) to 60:40 (v/v) for 40 minutes, using a flow rate of 1.0 mL/min. Ultraviolet (UV) analysis was performed at a wavelength of 227 nm. Biphenyl dimethyl dicarboxylate was used for the internal standard.

While the following examples are provided for the purpose of illustrating certain aspects of the present invention, they are not to be construed as limiting the scope of the appended claims.

Examples

Preparation Example 1a

A diblock copolymer of monomethoxy polyethylene glycol and polylactide having a benzoyloxy terminal group. (mPEG—PLA—Bz)

25 grams of monomethoxy polyethylene glycol (mPEG with a molecular weight of 2,000) and DL-lactide which was recrystallized from ethyl acetate, and 0.25 g of stannous octoate which was dissolved in 5 mL toluene, were added to a reactor equipped with a mechanical stirrer and a distillation set. Excess toluene was evaporated at 120° C. The polymerization reaction was carried out under vacuum (25 mmHg) for 6 hours. The vacuum was released and 50 mL benzoyl chloride was added to cause substitution of the hydrogen atom of the terminal hydroxyl group by a benzoyl group. The reaction mixture was then agitated for 5 hours at 100° C. The reaction product was dissolved in chloroform and poured into cold diethyl ether (4° C.) to precipitate the polymer. The precipitated polymer was washed twice with diethyl ether and dried under vacuum (0.1 mmHg) for 24 hours. The molecular weight of the block copolymer (mPEG—PLA—Bz) was determined by nuclear magnetic resonance (NMR) spectroscopy. The NMR spectrum is as shown in FIG. 1.

Preparation Example 1b

A diblock copolymer of monomethoxy polyethylene glycol and polyactide having a benzoyloxy terminal group (mPEG—PLA—Bz)

25 grams monomethoxy polyethylene glycol (mPEG with a molecular weight of 2,000) and DL-lactide which was recrystallized from ethyl acetate, and 0.25 g of stannous octoate which was dissolved in toluene (5 mL), were added to a reactor equipped with a mechanical stirrer and a distillation set. Excess toluene was evaporated at 120° C. The polymerization reaction was carried out under vacuum (25 mmHg) for 6 hours. The reaction product was dissolved in chloroform and poured into cold diethyl ether (4° C.) to precipitate the polymer. The precipitated polymer (mPEG—PLA) was washed twice with diethyl ether and dried under vacuum (0.1 mmHg) for 24 hours.

In order to substitute the hydrogen atom of the terminal hydroxyl group with a benzoyl group, the above-obtained polymer (mPEG—PLA) (30 g) and benzoyl chloride (60 mL) were added into a reactor and agitated for 5 hours at 100° C. The reaction product was dissolved in chloroform and poured into cold diethyl ether (4° C.) to precipitate the polymer. The precipitated polymer was washed twice with diethyl ether and dried under vacuum (0.1 mmHg) for 24 hours. The molecular weight of the block copolymer (mPEG—PLA—Bz) was determined by nuclear magnetic resonance (NMR) spectroscopy. The NMR spectrum is as shown in FIG. 1.

Preparation Example 2

Figure 2:
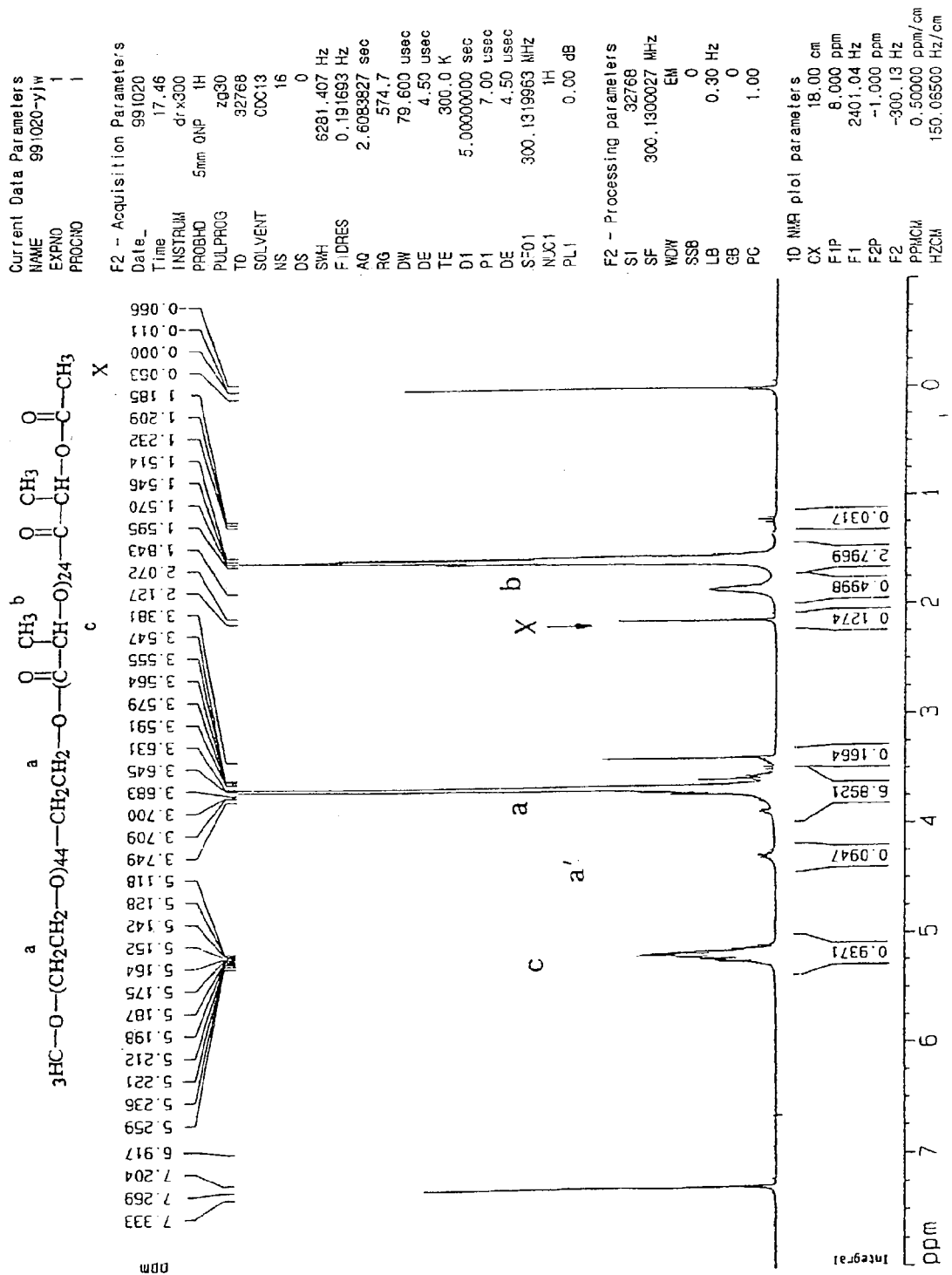
FIG. 2 is the NMR spectrum of mPEG—PLA—Ac.

A diblock copolymer of monomethoxy polyethylene glycol and polylactide having an acetyloxy terminal group A diblock copolymer (mPEG—PLA—Ac) was prepared using acetyl chloride (50 mL) instead of benzoyl chloride, added to cause substitution of the hydrogen atom of the terminal hydroxyl group by a acetyl group. The molecular weight was determined by the same procedure described in preparation Example 1a. The NMR spectrum is as shown in FIG. 2.

Comparative Preparation Example 1

A diblock copolymer of monomethoxy polyethylene glycol and polylactide.

Figure 3:
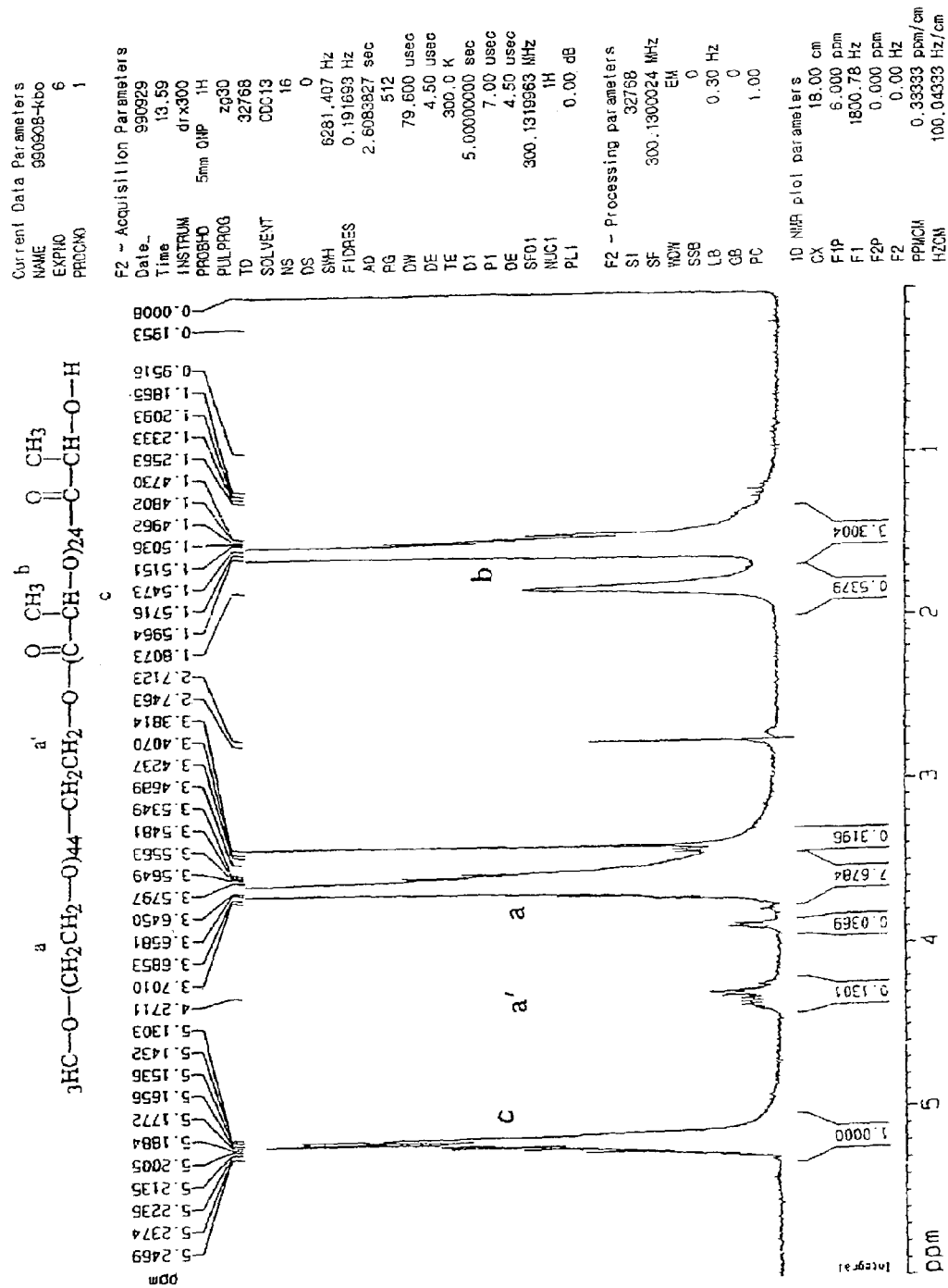
FIG. 3 is the NMR spectrum of mPEG—PLA.

25 grams of monomethoxy polyethylene glycol (mPEG with a molecular weight (mw) of 2,000) and DL-lactide which was recrystallized from ethyl acetate, and 0.25 grams of stannous octoate which was dissolved in 5 mL toluene, were added to a reactor equipped with a mechanical stirrer and a distillation set. Excess toluene was evaporated at 120° C. The polymerization reaction was carried out under vacuum (25 mmHg) for 6 hours. The reaction product was dissolved in chloroform and poured into cold diethyl ether (4° C.) to precipitate the polymer. The precipitated polymer was washed twice with diethyl ether and dried under vacuum (0.1 mmHg) for 24 hours. The molecular weight of the block copolymer (mPEG—PLA) was determined by nuclear magnetic resonance (NMR) spectroscopy. The NMR spectrum is as shown in FIG. 3.

Examples 1a~2

Stability of the Composition in Infusion Fluid

The polymers (190 mg) prepared in Examples 1a, 1b, and 2, were dissolved in acetonitrile (2 mL). Paclitaxel (10 mg), which was dissolved in acetonitrile (1 mL), was mixed with the polymer solution. A homogeneous drug-polymer matrix was obtained by evaporating the organic solvent at 60° C. under nitrogen flow followed by vacuum (0.1 mmHg) drying for 24 hours. The aqueous micellar solution was prepared by dissolving the drug-polymer matrix in distilled water (2 mL). The solution was then freeze-dried at −50° C. for 24 hours.

In order to dilute the formulation to a concentration for infusion (paclitaxel concentration of 1.0 mg/mL), the freeze-dried composition (100 mg), prepared as described above, and saline (5 mL) were added to a vial and mixed with a Vortex Mixer. This diluted solution was then placed in a thermostat at 25° C. At given time intervals, a 0.2 mL solution was removed by a syringe and filtered through a 0.45 μm PVDF syringe filter (Milipore, Cat No. SLHV004NL). The drug concentration in the solution was then determined by HPLC assay as described above. The results are shown in Table 1.

Comparative Example 1

The freeze-dried compositions and micellar solutions were prepared by the same procedure as described in Example 1, using the polymers prepared in comparative Example 1. The results of the stability test are shown in Table 1.

Comparative Example 2

(Taxol® Formulation)
Taxol® (Britol-Myers Squibb) formulation was diluted to a concentration suitable for infusion (paclitaxel concentration of 1.0 mg/mL) in normal saline, and the stability test was carried out by the same procedure as described in Example 1. The results are shown in Table 1.

TABLE 1

Stability of the Composition in Infusion Fluid (1.0 mg/mL) at 25° C.

| No. | | Polymer | 0 hr | 24 hr | 48 hr | 72 hr |
|---|---|---|---|---|---|---|
| Example | 1a | mPEG-PLA-Bz | 100 | 100 | 99.3 | 98.7 |
| | 1b | mPEG-PLA-Bz | 100 | 100 | 99.5 | 98.7 |
| | 2 | mPEG-PLA-Ac | 100 | 99.5 | 98.7 | 97.5 |
| Comparison | 1 | mPEG-PLA | 100 | 98.0 | 75.3 | 62.4 |
| | 2 | Cremophor EL[a] | 100 | 95.0 | 82.7 | 67.0 |

[a] Test was carried out using Taxol ® (Britol-Myers Squibb) formulation.

As shown in Table 1, when the paclitaxel was incorporated in the composition employing a polymer with a functional group at its end having chemical attraction to it, more than 90% of the drug remained incorporated in the polymeric micelles at a concentration in the infusion fluid of (1.0 mg/mL) for 3 days at 25° C., while less than 70% of the drug remained in the case of the Taxol® (Britol-Myers Squibb) formulation containing Cremophor EL or the compositions not employing the functional groups.

Examples 3~4

Stability of the Composition at a Plasma Concentration 0.5 mL of the aqueous micellar solutions prepared in Example 1a and 2 were diluted with normal saline (12.5 mL) to give a paclitaxel concentration of 0.04 mg/mL, which is below the plasma concentration when administered by one bolus iv injection at the normal dose of paclitaxel (175 mg/m$^2$). This diluted solution was then placed in a thermostat at 37° C. At given time intervals, a 0.5 mL sample was removed by a syringe, and filtered through a 0.45 μm PVDF syringe filter (Milipore, Cat No. SLHV004NL). The drug concentration in the solution was then determined by HPLC assay as described above. The results are shown in Table 2.

Comparative Example 3

The stability test was carried out by the same procedure as described in Example 3, using the aqueous micellar solution prepared in Comparative Example 1. The results are shown in Table 2.

Comparative Example 4

(Taxol® Formulation)
A Taxol® (Britol-Myers Squibb) formulation was diluted in normal saline to a concentration of 0.04 mg/mL, and the stability test was carried out by the same procedure as described in Example 3. The results are shown in Table 2.

TABLE 2

Stability at a plasma concentration (paclitaxel 0.04 mg/mL), 37° C.

| No. | | Polymer | 0 hr | 6 hr | 12 hr | 24 hr | 48 hr | 72 hr |
|---|---|---|---|---|---|---|---|---|
| Exa- | 3 | mPEG-PLA-Bz | 100 | 100 | 100 | 100 | 100 | 95.6 |
| mple | 4 | mPEG-PLA-Ac | 100 | 100 | 100 | 100 | 100 | 94.2 |

TABLE 2-continued

Stability at a plasma concentration (paclitaxel 0.04 mg/mL), 37° C.

| No. | | Polymer | Remained Drug (%) | | | | | |
|---|---|---|---|---|---|---|---|---|
| | | | 0 hr | 6 hr | 12 hr | 24 hr | 48 hr | 72 hr |
| Com- | 3 | mPEG-PLA | 100 | 91.6 | 54.5 | 36.8 | 29.1 | 25.6 |
| parison | 4 | CremophorEL[a)] | 100 | 90.3 | 58.0 | 43.5 | 31.8 | 27.7 |

[a)]Test was carried out using Taxol ® (Britol-Myers Squibb) formulation.

As shown in Table 2, the formulation of the present invention exhibited improved stability at a concentration below the initial drug plasma concentration corresponding to one bolus iv injection of a normal dose of paclitaxel (175 mg/m$^2$).

Examples 5~6

Paclitaxel Plasma Concentration in Rat

Paclitaxel compositions for injection were prepared by dissolving the freeze-dried compositions prepared in Examples 1a and 2 in normal saline to give a concentration of 1.0 mg/mL. According to the procedure described in the pharmacokinetic experiment, the compositions were injected into the tail vein of Sprague-Dawley rats having body weights of 200~250 g, with the dose of paclitaxel being 20 mg/kg. At given line intervals, blood samples were drawn in heparinized tubes from the tail vein. The drug plasma concentration was determined by HPLC according to the above-described procedure and the results are shown in Table 3.

Comparative Example 5

The pharmacokinetic experiments were carried out by the same procedure as described in Example 5, using the aqueous micellar solution prepared in the Comparative Example 1. The results are shown in Table 3.

Comparative Example 6

(Taxol® formulation)
A Taxol® (Britol-Myers Squibb) formulation was diluted to a concentration of 1.0 mg/mL in normal saline, and the pharmacokinetic experiment was carried out by the same procedure described in Example 5. The results are shown in Table 3.

TABLE 3

Paclitaxel Plasma Concentration in Rat

| No. | | Polymer | Paclitaxel Plasma Concentration (μg/mL) | | | | |
|---|---|---|---|---|---|---|---|
| | | | 3 min | 30 min | 120 min | 240 min | 360 min |
| Example | 5 | mPEG-PLA-Bz | 212.2 | 61.9 | 20.7 | 6.1 | 2.4 |
| | 6 | mPEG-PLA-Ac | 175.8 | 47.3 | 14.5 | 5.0 | 2.1 |
| Comparison | 5 | mPEG-PLA | 40.6 | 23.4 | 7.4 | 2.2 | 0.1 |
| | 6 | Cremophor EL[a)] | 105.5 | 43.0 | 13.8 | 5.3 | 2.1 |

[a)]Test was carried out using Taxol ® (Britol-Myers Squibb) formulation.

As shown in Table 3, the formulation of the present invention exhibited, in rats, superior drug plasma concentrations compared to the Taxol® formulation or the compositions not employing hydrophobic groups at the ends of polymer. In other words, the formulation of the present invention provides for improved bioavailability of paclitaxel when administered by intravenous infusion.

While the invention has been described with respect to the above specific embodiments, it should be recognized that various modifications and changes may be made to the invention by those skilled in the art which also fall within the scope of the invention as defined by the appended claims. It is to be understood that the above examples are illustrative of application of the principles of the present invention. Numerous modifications and alternative arrangements can be devised without departing from the spirit and scope of the present invention. The present invention has been described above in connection with the exemplary embodiments(s) of the invention. It will be apparent to those of ordinary skill in the art that numerous modifications can be made without departing from the principles and concepts of the invention as set forth in the claims.

What is claimed is:

1. A composition capable of forming a polymeric micelle in a body fluid or an aqueous medium, said composition comprising an amphiphilic block copolymer having a hydrophilic A block component and a hydrophobic biodegradable B block component, wherein the hydrophobic biodegradable B block component of the copolymer is capped with an acyl group or carbamyl group of $C_1$ to $C_9$ alkyl, aryl, alkaryl or aralkyl group.

2. The composition of claim 1, wherein the amphiphilic block copolymer is selected from the group consisting of AB diblock and BAB triblock copolymers.

3. The composition of claim 1, wherein the amphiphilic block copolymer is represented by formula (I) below:

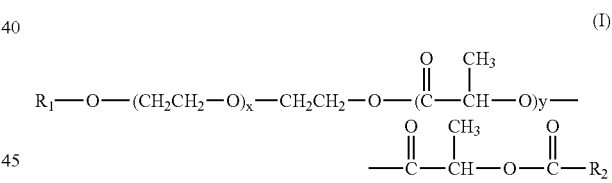

(I)

wherein x is an integer of 20–300, and y is an integer of 15–70, $R_1$ is H, a $C_1$ to $C_4$ alkyl, a $C_1$ to $C_4$ acyl or is represented by formula (II):

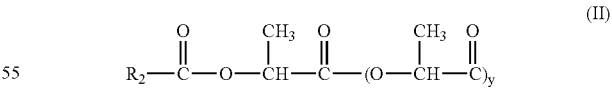

(II)

wherein $R_2$ is a $C_1$ to $C_9$ alkyl, aryl, alkaryl or aralkyl group, or NH—$R_3$ wherein $R_3$ is a $C_1$ to $C_9$ alkyl, aryl, alkaryl or aralkyl group, x is an integer of 20–300, and y is an integer of 15–70.

4. The composition of claim 3, wherein $R_2$ is a member selected from the group consisting of methyl, ethyl, propyl and butyl.

5. The composition of claim 3, wherein R2 is a phenyl group or a heterocyclic group selected from the group consisting of thienyl, furyl, pyridinyl groups.

6. The composition of claim 3, wherein R2 is a benzyl group.

7. The composition of claim 3, wherein R2 is a tolyl group.

8. The composition of claim 3, wherein R1 is a methyl group and R2 is a methyl, phenyl or enthylamino group.

9. The composition of claim 2, wherein the hydrophilic A block component is within a range of 40 to 80 wt % based on total weight of the block copolymer.

10. The composition of claim 2, wherein the hydrophilic A block component is poly(ethylene glycol) or monomethoxy poly(ethylene glycol).

11. The composition of claim 1, wherein the block copolymer has an average molecular weight of from 1,000 to 15,000 Daltons.

12. The composition of claim 1, wherein the hydrophobic biodegradable polymer B block component is selected from the group consisting of a polylactide, copolymer of lactide and glycolide, a copolymer of caprolactone and glycolide, polycaprolactone, a polyanhydride, a polyorthoester, a copolymer of lactide and 1,4-dioxan-2-one, and a copolymer of caprolactone and 1,4-dioxan-2-one.

13. A hydrophobic drug containing polymeric composition capable of forming stable polymeric micelles in an aqueous environment, said composition comprising a hydrophobic drug and a composition of claim 1, wherein in an aqueous environment said drug is physically entrapped within, but not covalently bound to, a hydrophobic core formed by the hydrophobic B block component and its terminal hydrophobic group.

14. The composition of claim 13, wherein the content of the hydrophobic drug is up to 50 wt % based on the total weight of the block copolymer and the drug.

15. The composition of claim 13, wherein the hydrophobic drug has a solubility of less than 10 mg/mL.

16. The composition of claim 13, wherein the hydrophobic drug is selected from the group consisting of anticancer agents, antifungal agents, steroids, antiinflammatory agents, sex hormones, immunosuppressants, antiviral agents, anesthetics, antiemetics, and antihistamine agents.

17. The composition of claim 13, wherein the hydrophobic drug is selected from the group consisting of a taxane analog, camptothecin, doxorubicin, cisplatin, 5-fluorouracil, cyclosporine A, amphotericin B, itraconazole, ketoconazole, indomethacin, testosterone, estradiol, dexamethasone, prednisolone, and triamcinolone acetonide.

18. The composition of claim 17, wherein the hydrophobic drug is a taxane analog.

19. The composition of claim 18, wherein the taxane analog is paclitaxel.

20. An aqueous formulation for parenteral administration of a taxane analog comprising the composition according to claim 18, which is dissolved in an aqueous medium and has a concentration of the taxane analog in the range of 0.1~3 mg/mL.

21. The aqueous formulation of claim 20, wherein the aqueous medium is a 0.9% sodium chloride water solution, 5% dextrose water solution, 5% dextrose and 0.9% sodium chloride water solution, or a 5% dextrose Ringer's solution.

22. A method of preparing the composition according to claim 13, which is capable of forming a stable polymeric micelle in aqueous environments, comprising the steps of:
a) preparing a drug-polymer mixture by dissolving the amphiphilic block copolymer of claim 1 and a hydrophobic drug in an organic solvent followed by evaporation of the solvent;
b) dissolving the drug-polymer mixture in an aqueous environment to obtain a stable micellar solution; and,
c) freeze-drying the aqueous micellar solution.

23. The method of claim 22, wherein the content of the hydrophobic drug is up to 50 wt % based on the total weight of the block copolymer and the drug.

24. The method of claim 22, wherein the hydrophobic drug has a solubility of less than 10 mg/mL.

25. The method of claim 24, wherein the hydrophobic drug is selected from the group consisting of a taxane analog, camptothecin, doxorubicin, cisplatin, 5-fluorouracil, cyclosporine A, amphotericin B, itraconazole, ketoconazole, indomethacin, testosterone, estradiol, dexamethasone, prednisolone, and triamcinolone acetonide.

26. The method of claim 25, wherein the hydrophobic drug is a taxane analog.

27. The method of claim 26, wherein the taxane analog is paclitaxel.

28. A hydrophobic drug containing polymeric composition capable of forming stable polymeric micelles in an aqueous environment, said composition comprising a hydrophobic drug and a composition of claim 3, wherein said drug is physically entrapped within, but not covalently bound to, a hydrophobic core formed by the hydrophobic B block component and its terminal hydrophobic group.

29. The composition of claim 28, wherein the content of the hydrophobic drug is up to 50 wt % based on the total weight of the block copolymer and the drug.

30. The composition of claim 28, wherein the hydrophobic drug has a solubility of less than 10 mg/mL.

31. The composition of claim 28, wherein the hydrophobic drug is selected from the group consisting of anticancer agents, antifungal agents, steroids, antiinflammatory agents, sex hormones, immunosuppressants, antiviral agents, anesthetics, antiemetics, and antihistamine agents.

32. The composition of claim 28, wherein the hydrophobic drug is selected from the group consisting of a taxane analog, camptothecin, doxorubicin, cisplatin, 5-fluorouracil, cyclosporine A, amphotericin B, itraconazole, ketoconazole, indomethacin, testosterone, estradiol, dexamethasone, prednisolone, and triamcinolone acetonide.

33. The composition of claim 32, wherein the hydrophobic drug is a taxane analog.

34. The composition of claim 33, wherein the taxane analog is paclitaxel.

35. An aqueous formulation for parenteral administration of a taxane analog comprising the composition according to claim 33, which is dissolved in an aqueous medium and has a concentration of the taxane analog in the range of 0.1~3 mg/mL.

36. The aqueous formulation of claim 35, wherein the aqueous medium is a 0.9% sodium chloride water solution, 5% dextrose water solution, 5% dextrose and 0.9% sodium chloride water solution, or a 5% dextrose in Ringer's solution.

37. A method of preparing the composition according to claim 28, which is capable of forming a stable polymeric micelle in aqueous environments, comprising the steps of: a) preparing a drug-polymer mixture by dissolving the amphiphilic block copolymer of claim 3 and a hydrophobic drug in an organic solvent followed by evaporation of the solvent; b) dissolving the drug-polymer mixture in an aqueous environment to obtain a stable micellar solution; and,
c) freeze-drying the aqueous micellar solution.

38. The method of claim 37, wherein the content of the hydrophobic drug is up to 50 wt % based on the total weight of the block copolymer and the drug.

39. The method of claim 37, wherein the hydrophobic drug has a solubility of less than 10 mg/mL.

40. The method of claim 39, wherein the hydrophobic drug is selected from the group consisting of a taxane analog, camptothecin, doxorubicin, cisplatin, 5-fluorouracil, cyclosporine A, amphotericin B, itraconazole, ketoconazole, indomethacin, testosterone, estradiol, dexamethasone, prednisolone, and triamcinolone acetonide.

41. The method of claim 37, wherein the hydrophobic drug is a taxane analog.

42. The method of claim 38, wherein the taxane analog is paclitaxel.

* * * * *